US010745450B2

(12) United States Patent
Paetzold et al.

(10) Patent No.: US 10,745,450 B2
(45) Date of Patent: Aug. 18, 2020

(54) PEPTIDES AND USES THEREOF

(71) Applicants: FUNDACIÓ CENTRE DE REGULACIÓ GENÒMICA (CRG), Barcelona (ES); INSTITUCIÓ CATALANA DE RECERCA I ESTUDIS AVANÇATS, Barcelona (ES)

(72) Inventors: Bernhard Paetzold, Magdeburg (DE); Maria Lluch Senar, Barcelona (ES); Luis Serrano Pubul, Barcelona (ES)

(73) Assignees: FUNDACIÓ CENTRE DE REGULACIÓ GENÒMICA (CRG), Barcelona (ES); INSTITUCIÓ CATALANA DE RECERCA I ESTUDIS AVANÇATS, Barcelona (ES)

( * ) Notice: Subject to any disclaimer, the term of this patent is extended or adjusted under 35 U.S.C. 154(b) by 0 days.

(21) Appl. No.: 15/553,552

(22) PCT Filed: Feb. 26, 2016

(86) PCT No.: PCT/EP2016/054065
§ 371 (c)(1),
(2) Date: Aug. 24, 2017

(87) PCT Pub. No.: WO2016/135281
PCT Pub. Date: Sep. 1, 2016

(65) Prior Publication Data
US 2018/0037613 A1   Feb. 8, 2018

(30) Foreign Application Priority Data
Feb. 27, 2015   (EP) ..................................... 15157028

(51) Int. Cl.
| C07K 14/30 | (2006.01) |
| C07K 14/47 | (2006.01) |
| C07K 14/81 | (2006.01) |
| C12N 9/88  | (2006.01) |
| A61K 38/00 | (2006.01) |

(52) U.S. Cl.
CPC .......... *C07K 14/30* (2013.01); *C07K 14/4746* (2013.01); *C07K 14/81* (2013.01); *C12N 9/88* (2013.01); *C12Y 402/02003* (2013.01); *A61K 38/00* (2013.01); *C07K 2319/036* (2013.01)

(58) Field of Classification Search
None
See application file for complete search history.

(56) References Cited

U.S. PATENT DOCUMENTS

2005/0288866 A1* 12/2005 Sachdeva ........... G01N 33/6803
702/19

FOREIGN PATENT DOCUMENTS

WO   WO 2010/061226 A1   6/2010

OTHER PUBLICATIONS

Sequence Alignment of SEQ ID No. 123 of US Patent Application No. 20050288866 with instant SEQ ID No. 1, Search conducted on Sep. 19, 2018, 1 page. (Year: 2018).*
Sequence Alignment of S73523 with instant SEQ ID No. 2, Search conducted on Sep. 19, 2018, 1 page (Year: 2018).*
Sequence Alignment of S73764 with instant SEQ ID No. 3, Search conducted on Sep. 19, 2018, 1 page (Year: 2018).*
Sequence Alignment of S62791 with instant SEQ ID No. 4, Search conducted on Sep. 19, 2018, 1 page (Year: 2018).*
Sequence Alignment of AAW19602 with instant SEQ ID No. 5, Search conducted on Sep. 19, 2018, 2 pages (Year: 2018).*
Sequence Alignment of SEQ ID No. 125 of US Patent Application No. 20050288866 with instant SEQ ID No. 6, Search conducted on Sep. 19, 2018, 1 page (Year: 2018).*
International Search Report and Written Opinion dated May 9, 2016 for PCT/EP2016/054065, 14 pages.
Boersema, Paul, et al., "Multiplex peptide stable isotope dimethyl labelling for quantitative proteomics" Nature Protocols, Mar. 19, 2009, vol. 4, No. 4, pp. 484-494.
Chopra-Dewasthaly, Rohini, et al., "First steps towards the genetic manipulation of *Mycoplasma agalactiae* and *Mycoplasma bovis* using the transposon Tn4001mod" Int. J. Med. Microbiology, Jan. 2005, vol. 294(7), pp. 447-453.
Greenberg-Ofrath, Noa, et al., "Cyclodextrins as carriers of cholesterol and fatty acids in cultivation of mycoplasmas" Applied and Environmental Microbiology, Feb. 1993, vol. 59, No. 2, pp. 547-551.
Kitamikado, Manabu, et al., "Method designed to detect alginate-degrading bacteria" Applied and Environmental Microbiology, Sep. 1990, vol. 56, No. 9, pp. 2939-2940.
Yus, Eva, et al., "Impact of genome reduction on bacterial metabolism and its regulation", Science, Nov. 27, 2009, vol. 326, pp. 1263-1268.
Database Uniprot:Q50341, XP-002741690, Nov. 1, 1997, 1 page.
Database Uniprot:P75152, XP-002741691, Nov. 1, 1997, 1 page.
Database Uniprot:Q50288, XP-002756430, Dec. 1, 2000, 1 page.
Database Uniprot:O07713, XP-002756431, Jul. 1, 1997, 1 page.
Database Uniprot:P75296, XP-002741696, Nov. 1, 1997, 1 page.

* cited by examiner

*Primary Examiner* — Channing S Mahatan
(74) *Attorney, Agent, or Firm* — Squire Patton Boggs (US) LLP

(57) ABSTRACT

The invention provides a series of peptide signals which, when linked to a polypeptide of interest (POI), ensure that said polypeptide is secreted in high yields by a host cell such as *Mycoplasma pneumoniae*. The invention also provides fusion proteins tagged with said peptide signals, the nucleic acid sequences coding for them, host cells comprising said tagged fusion proteins and a variety of uses of the fusion proteins and the host cells.

4 Claims, 5 Drawing Sheets
Specification includes a Sequence Listing.

PEPTIDES AND USES THEREOF

The present invention provides peptides which, when fused to a polypeptide of interest, drive the efficient secretion of the polypeptide of interest out of bacterial cells. The invention has multiple potential applications, in particular in the area of next-generation bacterial-based therapies.

BACKGROUND ART

Secretory protein expression is the expression of a protein in a host cell, where the protein is exported trough the cell membrane for its release into the extracellular medium or its displayed on the cell surface, anchored to the cell membrane. Secretory protein expression is mediated by a signal peptide at the N-terminus of the protein, which directs the extracellular export of the polypeptide.

Usually, recombinant proteins are intracellularly produced in prokaryotic hosts. When the protein is recovered in such a procedure, the cells have to be lysed which leads to a contamination of the recombinant protein with cellular content. The protein then has to be recovered from whole cell extracts in multi-step purification procedures, which is time consuming and results in poor yields. Also secreted proteins could be used for bacterial therapy where they target eukaryotic receptors on the target cells.

Secretion of recombinant proteins into the medium is a better strategy because purification of proteins from spent medium is easier and more compatible with continuous culturing.

Secretory protein expression has other uses. Examples of use for this type of protein expression include live-vaccine development, epitope mapping, biosorbent and biosensor development and the high throughput screening of protein and peptide libraries for drug discovery.

In secretion, recombinant proteins face the challenge of translocation across the complex cell envelope that consists of two lipid membranes (the inner and outer membrane) with a gel-like compartment, the periplasm, in between. This has been shown to be very difficult and the methods previously used have had low efficacy.

On the other hand, synthetic biology is based on engineering living organisms in order to exploit them in a myriad of applications ranging from biosensors and the production of biofuels to therapeutic treatments. Microorganisms have now long been used by the industry in the production of many therapeutic proteins. However, the fine tuning of a whole microorganism in terms of its genome by a synthetic biology approach opens up a way of exploiting the organism itself as a therapy or a therapeutic vehicle. One particularly exciting application is the possibility of creating bacterial factories that can live in diseased tissues and produce, display or secrete therapeutic proteins in situ.

In order to manipulate a host cell such as a bacterium and to turn it into a therapeutic vehicle, one must first have a very deep understanding about its genome, its proteome and all its metabolic processes. Currently a main bottleneck is the inability to predict with accuracy the behaviour of engineered bacteria. In order to minimize potential undesired effects in therapeutic applications, and with a goal of simplifying a very complex living system, some of the simplest bacteria are being studied as synthetic biology platforms.

Host bacteria can be engineered so that they synthesize a polypeptide of interest (POI) with therapeutic applications. With the goal of increasing the surface display to the exterior of the cell and/or their secretion to the outer medium, a series of strategies can be implemented. One of them is the coupling (fusion) in frame of the polypeptide of interest with a second peptide that promotes a variety of secretion processes within the host cell. Some peptides can drive POI's surface display in the extracellular section of the cell membrane. In this case, the POI can be used for eliciting an immune response via the display of a foreign protein to an immune system's machinery, and therefore the engineered bacteria carrying the fusion protein can be used as a vaccine. Some other peptides can drive the production and secretion of the fusion protein (POI-secretion enhancer) to the outer medium. In this latter case, the engineered bacteria can be used as a tissue delivery chassis of therapeutic proteins.

A range of references exist in the prior art that deal with peptides useful in surface displaying and secreting intended polypeptides. However, in spite of what is known in the field, there are many issues that still need to be addressed. The successful secretion of a polypeptide of interest by a host cell is still hindered by many factors such as: (a) the coupling of the secretion enhancer to the POI can alter the folding and final structure of either or both partners, with a subsequent change in their biological functions; and (b) the surface display and/or secretion yields are suboptimal in terms of real applicability for many bacterial host cells such as *Mycoplasma*.

Therefore, it is desirable to provide for other peptide secretion enhancers.

SUMMARY OF THE INVENTION

Inventors have found a series of secretion signal peptides that, when fused to a POI, drive its efficient secretion in a bacterial host, such as *Mycoplasma pneumoniae*, and do not interfere with their biological activity, as seen in the experimental data below. Surprisingly, inventors have found that these peptides are effective in secreting POIs with a very wide range of protein folds. This reveals that the signal peptides of the invention have a wide applicability spectrum in terms of secretion of POIs.

Due to this efficient secretion profile, the POI purification from the medium is easier and more compatible with continuous culturing.

Thus, a first aspect of the present invention is a peptide comprising a sequence which has at least 90% of homology with one of the sequences of the group consisting of:

```
Mpn 142 with sequence:
                                  SEQ ID NO: 1
MKSKLKLKRYLLFLPLLPLGTLSLANTY;

Mpn 645 with sequence:
                                  SEQ ID NO: 2
MKLKLKFLLISLLGSSLLLSACSSAATQ;

Mpn 400 with sequence:
                                  SEQ ID NO: 3
MKLNFKIKDKKTLKRLKKGGFWALGLFGAAINAFSAVL;

Mpn 200 with sequence:
                                  SEQ ID NO: 4
MKFKYGAIVFSGLLGVSAILAACGT;

Mpn 213 with sequence:
                                  SEQ ID NO: 5
MKLSAIISLSVAGTVGTTAVVVPTTITLVNK;

Mpn 489 with sequence:
                                  SEQ ID NO: 6
MGYKLKRWPLVAFTFTGIGLGVVLAACSALN;
```

The peptides of the invention can be either fused in frame directly to the POI, or can be fused with the POI via a linker.

The linker can have a series of properties. For instance, it can be a cleavage signal site which is the substrate of proteases, so that the cleavage of the POI and the peptides of the invention can be controlled under certain circumstances (presence or absence of the protease capable of processing the cleavage site) if it is needed.

As it is shown below, the peptide of the invention can be fused to a particular POI in order to efficiently secrete it in a particular bacterium. As it is illustrated below (see examples section and FIGS. 1 to 3), when a POI is endowed with a certain biological activity, the resulting fusion protein (POI-peptide of the invention) is also active. This is indicative that the peptide of the first aspect of the invention does not negatively affect the activity of the POI.

Therefore, in a second aspect the present invention provides a fusion protein comprising a polypeptide of interest (POI) and at least one peptide as defined in the first aspect of the invention, wherein the polypeptide of interest is heterologous to the at least one peptide.

A third aspect of the present invention is a nucleotide sequence coding for the peptide of the first aspect of the invention or the fusion protein of the second aspect of the invention.

Once the nucleotide sequence coding either the peptide of the first aspect or the fusion protein of the second aspect is generated, it is integrated in a suitable vector, which then is integrated in a host cell in order to express and secrete the desired fusion protein. Thus, a fourth aspect of the invention is a vector comprising the nucleotide sequence of the third aspect of the invention.

A fifth aspect of the invention is a host cell comprising the vector of the fourth aspect of the invention.

In addition, as it is illustrated in by the experimental data and the examples, once generated the fusion protein, the bacterium is able of efficiently secrete the active POI.

The modified host cell of the present invention, which has been engineered for expressing the fusion protein POI+ signal peptide of the invention, can be effectively used as a bacterial factory, which can live in diseased tissues and produce and secrete the active POI in situ. For this therapeutic in situ application, the host cell has to be selected from among those recognized as safe and non-toxic for humans and non-human animals. Alternatively, the cell can be engineered in order to make it safe and non-toxic. This therapeutic application is possible in cases where POI is a therapeutic peptide and the bacterial factory is used as a factory of the therapeutic protein.

If the host cell is engineered to be safe and non-toxic, it can itself be administered in the treatment of disease. The host cell can be engineered to be able to colonize and in if desired reproduce safely in a certain tissue, propagating in it and secreting the therapeutic fusion protein.

In a sixth aspect the present invention provides a pharmaceutical or veterinary composition comprising the fusion protein as defined in the second aspect of the invention or the host cell as defined in the fifth aspect of the invention, the host cell being safe and non-toxic for humans or non-human animals, together with pharmaceutically acceptable excipients or carriers.

In a seventh aspect the present invention provides the use of the peptide of the first aspect of the invention as secretion peptide of a polypeptide of interest (POI).

In an eighth aspect the present invention provides a fusion protein as defined in the second aspect of the invention or a host cell as defined in the fifth aspect of the invention, the host cell being safe and non-toxic for human or non-human animals, for use in therapy.

In an ninth aspect the invention provides a method for secretory protein expression of a fusion protein as defined in the second aspect of the invention, comprising the steps of: (a) providing a host cell according to the fifth aspect of the invention; and (b) inducing expression of the fusion protein.

Figure 1:
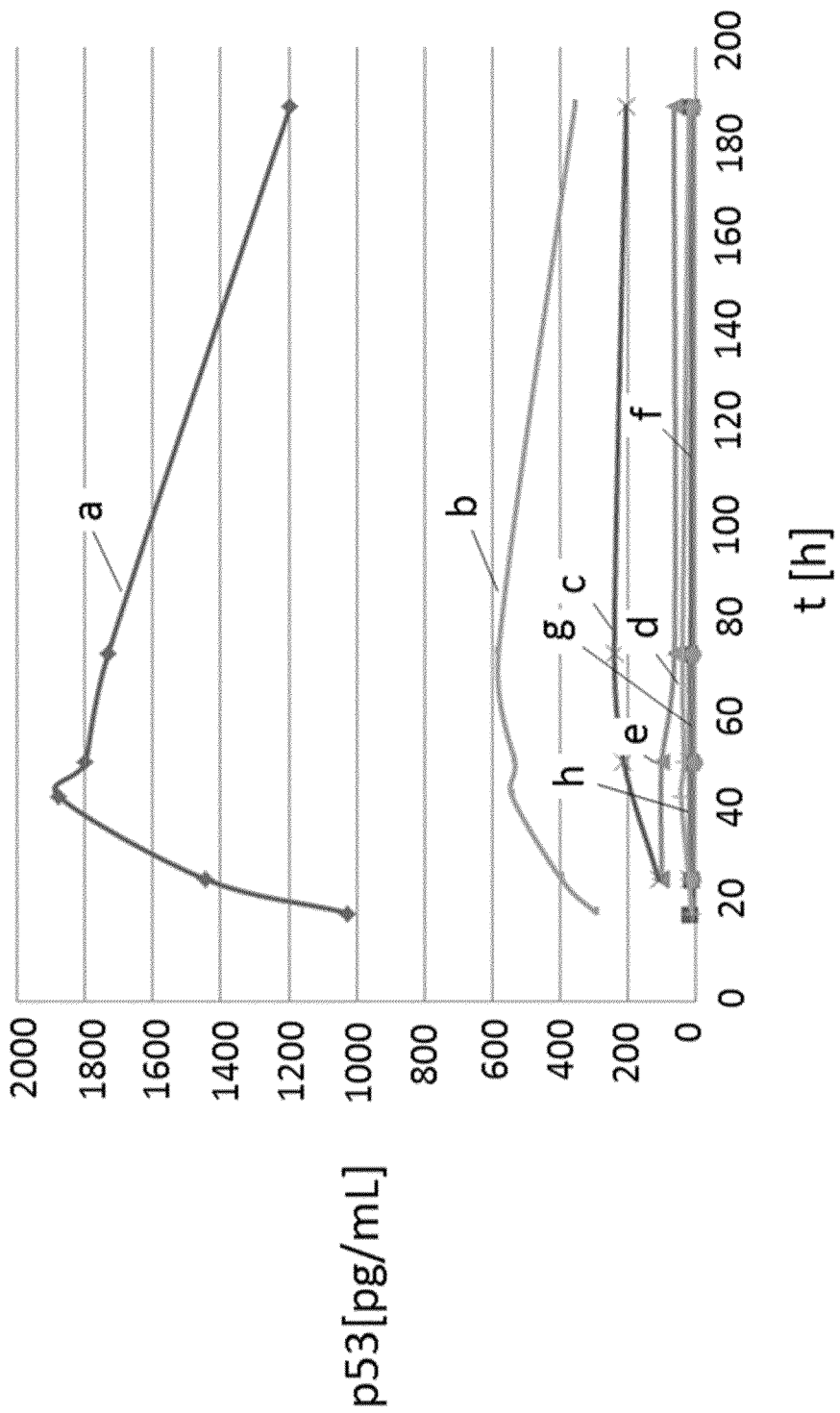
FIG. 1 Represents the secretion of p53 by different modified *M. pneumoniae* (a=Mpn-142-p53, b=Mpn-645-p53, c=Mpn-400-p53, d=Mpn-459-p53, e=Mpn-332-p53, f=Mpn-200-p53, g=Mpn-506-p53, h=Mpn-489-p53) into McCoy Media. X-axis=time after inoculation (t) expressed in hours; Y=concentration of p53 (pg/mL). The amounts were determined using a Roche p53 pan ELISA sandwich assay.

FIG. 2 Represents a bar-representation showing the alginate lyase activity assay in full medium supernatant from cultures secreting alginate lyase (M129 strain). All cultures were normalized to the same inoculation count at day 0 (bar "a") and over the next 5 days samples of the media were taken (bar "b"=sample taken at day 1, bar "c"=sample taken at day 2, and bar "d"=sample taken at day 5). The assay is based on the degradation of polymeric alginate to shorter sugar fragments.

FIG. 3_(A) represents the amount of secreted A1AT (ng/mL) by different strains of *M. pneumoniae* (specified in X-axis) cultivated in minimal medium (grey bar) or full Hayflick Media (black bar); (B) shows a neutrophil elastase activity assay (Y-axis, in rfu) using concentrated minimal media supernatant culture from MP WT and MP142 strains: A=Media Control, B=Concentrated *M. pneumoniae* supernatants, C=Reaction buffer only, (1)=NE (8 nM), (2)=NE+ A1AT, (3)=MP-WT, (4)=MP142; (c) shows a neutrophil elastase activity absorbance (N.E.A.A.) using purified A1AT from MP142 strain and purified A1AT from *E. Coli* (Acrys). Stripped bars and thick bars represent different biological replicas.

DETAILED DESCRIPTION OF THE INVENTION

As mentioned above, a first aspect of the invention is a peptide comprising a sequence having at least 90% of homology with one of the sequences of the group consisting of: SEQ ID NO: 1; SEQ ID NO: 2; SEQ ID NO: 3; SEQ ID SEQ ID NO: 4; SEQ ID NO: 5; SEQ ID NO: 6.

In the context of the invention, the term "signal peptide", also referred to as "secretion enhancer", is a short peptide (from 5 to 30 amino acids long) which is fused to the POI and allows the secretion of a particular POI to the extracellular medium.

In one embodiment of the first aspect of the invention the peptide comprises a sequence having at least 90% of identity with one of the sequences of the group consisting of: SEQ ID NO: 1; SEQ ID NO: 2; SEQ ID NO: 3; SEQ ID NO: 4; SEQ ID NO: 5; SEQ ID NO: 6.

The "percentage of homology"_between two amino acid sequences or two nucleotide sequences is to be understood as the percentage of identical sequence positions or replaced with other amino acids with side chains of similar features (i.e. polar, non-polar, with amino groups, with —SH groups), or other nucleotides, according to the broadly accepted classifications known by an expert in the field. The "percentage of identity" between two amino acid sequences or two nucleotide sequences is to be understood as the percentage of the sequence positions with identical amino acids or nucleotides. The percentage of homology and of identity between sequences may be calculated by means of "sequence alignment". The sequence alignment may be local or global. In the sense of the present invention the percentage of homology and of identity will be calculated, preferably, over a global alignment, among the entire sequence or an entire active fragment of the sequence. Global alignments are more useful when the sequences are similar and have approximately the same size (length). There are several algorithms available in the state of the art for performing these global alignments. There are also bioinformatics tools using such algorithms to obtain the percentage of identity and homology between sequences. As an example, global alignment between sequences may be performed by means of the well-known GGSEARCH or GLSEARCH software.
Figure 2:
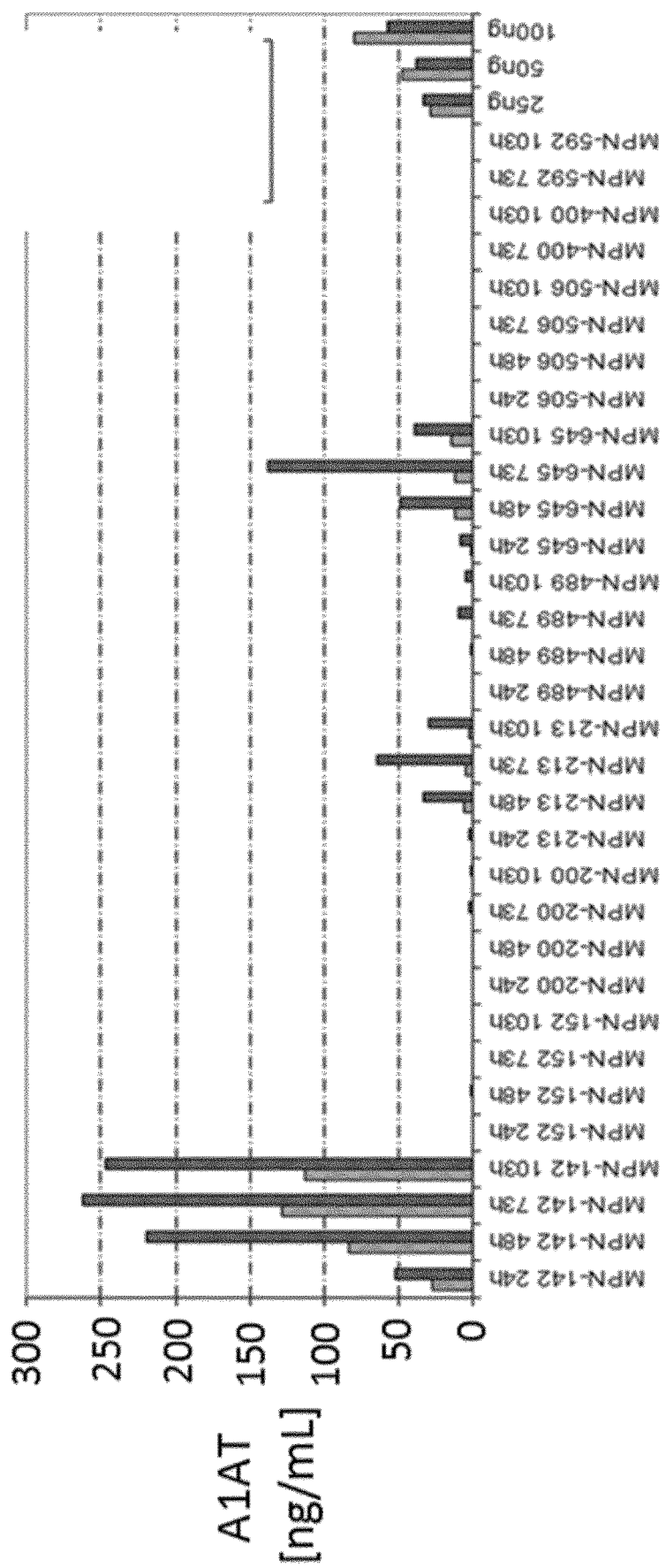
Figure 3A:
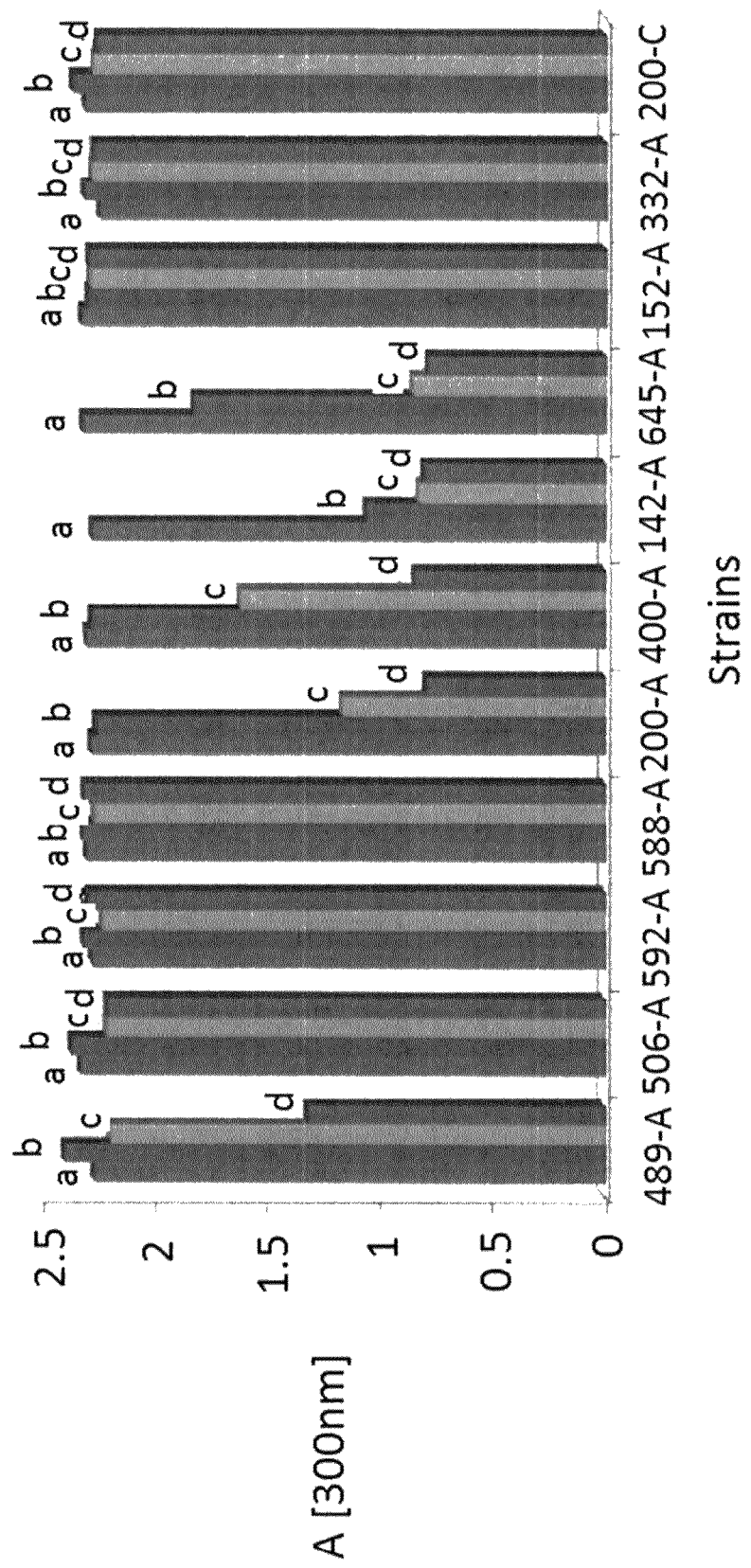
Figure 3B:
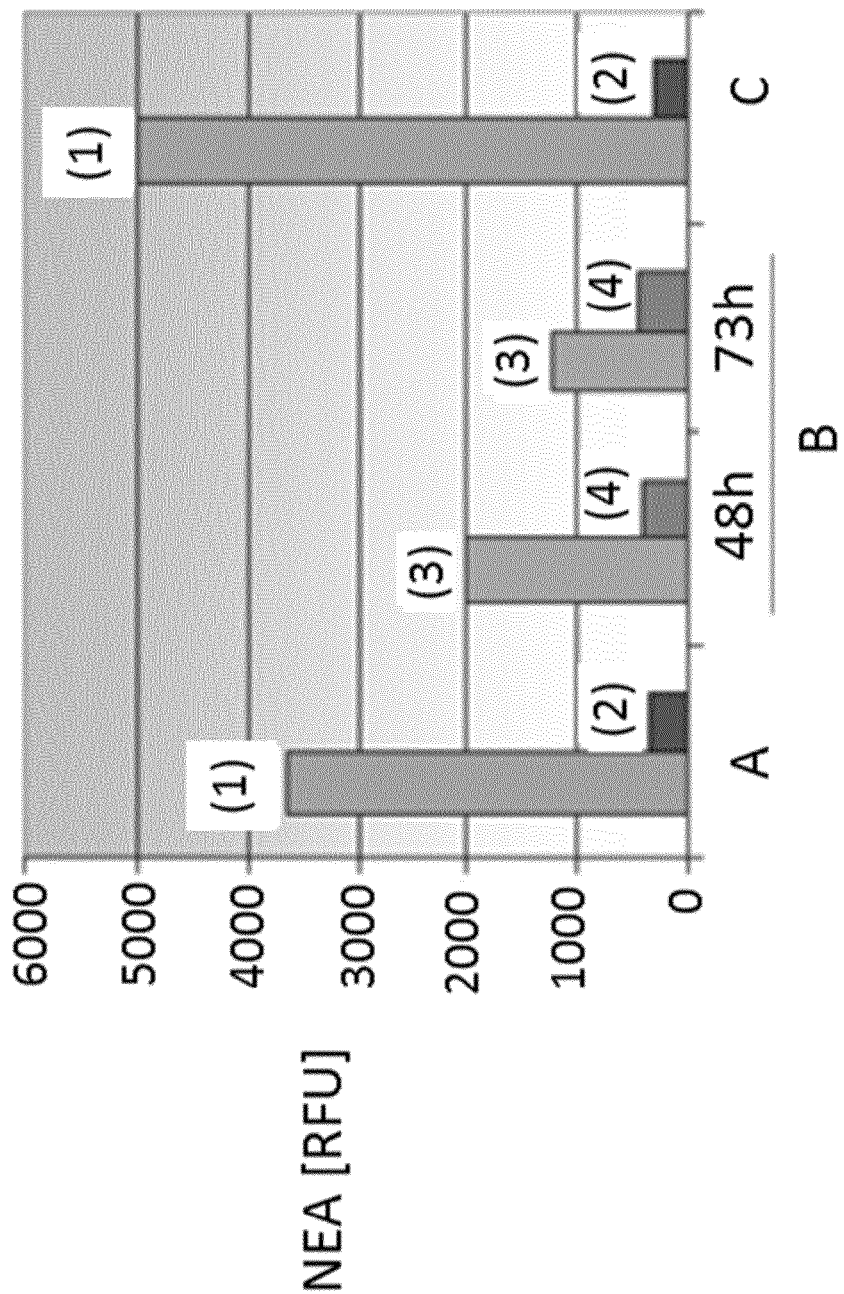
Figure 3C:
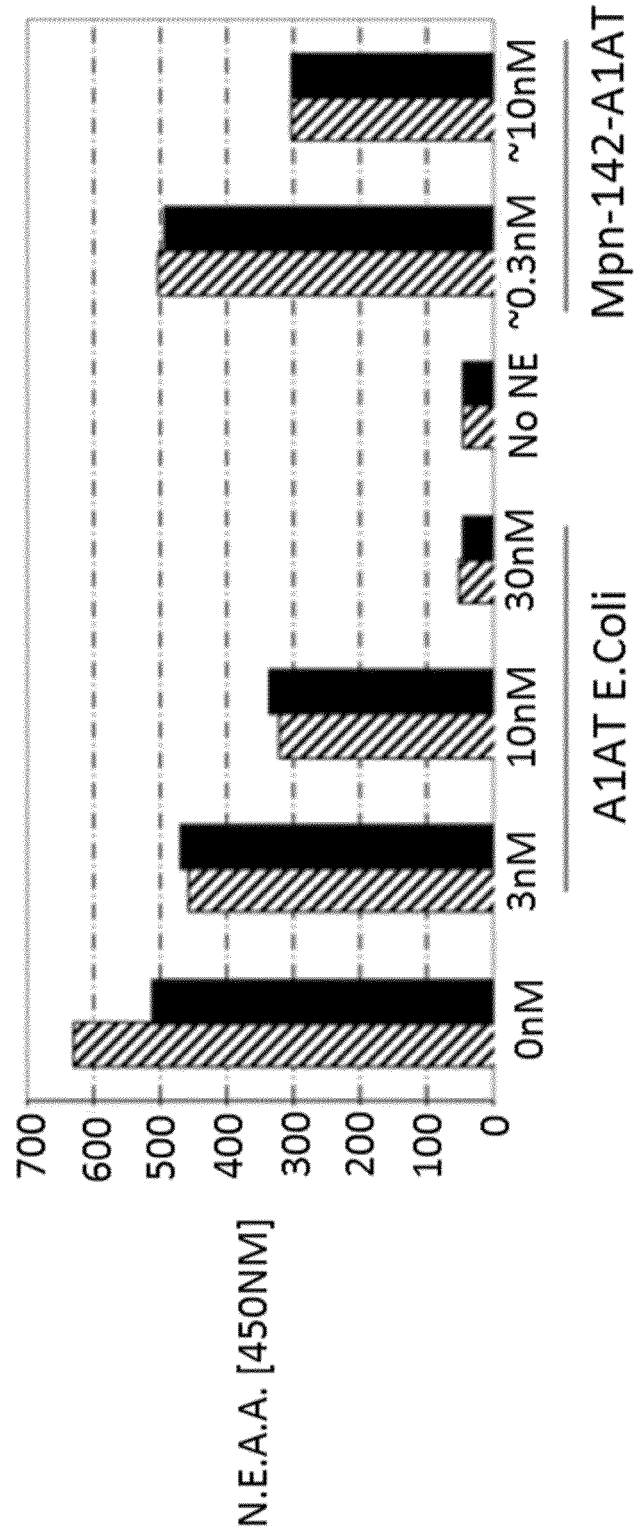

In another embodiment of the first aspect of the invention the peptide is one consisting in a sequence having at least 90% of homology with one of the sequences of the group consisting of: SEQ ID NO: 1; SEQ ID NO: 2; SEQ ID NO: 3; SEQ ID NO: 4; SEQ ID NO: 5; SEQ ID NO: 6.

In another embodiment of the first aspect of the invention the peptide is one consisting in a sequence having at least 90% of identity with one of the sequences of the group consisting of: SEQ ID NO: 1; SEQ ID NO: 2; SEQ ID NO: 3; SEQ ID NO: 4; SEQ ID NO: 5; SEQ ID NO: 6.

In still another embodiment the % of homology is of at least 90, 91, 92, 93, 94, 95, 96, 97, 98, 99 or 100.

In still another embodiment the % of identity is of at least 90, 91, 92, 93, 94, 95, 96, 97, 98, 99 or 100.

In one embodiment the peptide consists of a sequence which is one of the sequences of the group consisting of: SEQ ID NO: 1; SEQ ID NO: 2; SEQ ID NO: 3; SEQ ID NO: 4; SEQ ID NO: 5; SEQ ID NO: 6.

In another embodiment of the first aspect of the invention, the peptide comprises or consists of the sequence SEQ ID NO: 1, SEQ ID NO: 2; SEQ ID NO: 3. Advantageously, these peptides are the ones giving the most efficient results in terms of secretion of the active POI, as shown in the experimental data found below.

In a second aspect, the present invention provides a fusion protein comprising at least one POI together with a peptide as defined in the first aspect of the invention.

The term "fusion protein" as used herein is the result of in frame coupling of a polypeptide of interest (POI) through either its N- or C-terminal end to a peptide of the first aspect of the invention.

The term "polypeptide of interest" or simply POI, as used herein, is a polypeptide that the user of the invention wants a host cell to secrete in soluble form into the medium. Typically, the POI is a protein that the user wants to have secreted, whereas the signal peptide of the fusion protein assists in the secretion process. Typically, the POI is also heterologous to the signal peptide to which it is fused, which means that the POI does not originate from the same species as the signal peptide.

In one embodiment of the second aspect of the invention, the fusion protein comprises from 1 to 12 POIs. In another embodiment of the second aspect of the invention, the fusion protein comprises from 1 to 5 POIs. In still another embodiment of the second aspect of the invention, the fusion protein comprises 1 POI.

In one embodiment of the second aspect of the invention, POI has a therapeutic effect such that, when administered in a therapeutically effective amount to a patient suffering from a disease, it has a beneficial effect on the health and well-being of the patient, either curing the disease, slowing the progress of the disease; causing the disease to regress; alleviating one or more symptoms of the disease; preventing the occurrence of a disease or disorder; retarding the recurrence of the disease or disorder; or protecting against the onset of the disease.

Illustrative non-limitative examples of therapeutic POIs are antiproliferative agents, antiinflammatory agents, antineoplastic agents, antimitotic agents, antiplatelet agents, anticoagulant agents, antifebrin agents, antithrombin agents, cytostatic agents, antibiotics, angiogenic agents, hormones, and antigens. Alternatively, the POI can be a non-therapeutic polypeptide, such as an enzyme with a particular industrial interest (such as in fermentation processes, catalysis, etc.).

In another embodiment the POI is p53, Alginate Lyase A1-III or a1-antitrypsin.

In another embodiment of the second aspect of the invention, the N-terminal end of the POI is bound to the peptide of the first aspect of the invention through a peptide linker. This linker (or "spacer") makes it more likely that POI and signal peptide fold independently and behave as expected; i.e., incorporating a linker it is guaranteed that POI retains its function. In addition, this linker can be a cleavage signal site which is the substrate of proteases, so that the cleavage of the POI and the peptides of the invention can be controlled under certain circumstances (presence or absence of the protease capable of processing the cleavage site) if it is needed.

The terms "peptide linker" and "linker" are used interchangeably, and has to be understood as any amino acid sequence comprising from 1 to 100 amino acids, such sequence not negatively affecting neither POI's activity nor signal peptide function as displaying or secreting tool.

In another embodiment of the second aspect of the invention, the peptide comprises a sequence having at least 90% of homology with one of the sequences of the group consisting of: SEQ ID NO: 1; SEQ ID NO: 2; SEQ ID NO: 3; SEQ ID NO: 4; SEQ ID NO: 5; SEQ ID NO: 6. In another embodiment of the second aspect of the invention, the peptide comprises a sequence having at least 90% of identity with one of the sequences of the group consisting of: SEQ ID NO: 1; SEQ ID NO: 2; SEQ ID NO: 3; SEQ ID NO: 4; SEQ ID NO: 5; SEQ ID NO: 6. In another embodiment of the second aspect of the invention the peptide is one consisting in a sequence having at least 90% of homology with one of the sequences of the group consisting of: SEQ ID NO: 1; SEQ ID NO: 2; SEQ ID NO: 3; SEQ ID NO: 4; SEQ ID NO: 5; SEQ ID NO: 6. In another embodiment of the second aspect of the invention the peptide is one consisting in a sequence having at least 90% of identity with one of the sequences of the group consisting of: SEQ ID NO: 1; SEQ ID NO: 2; SEQ ID NO: 3; SEQ ID NO: 4; SEQ ID NO: 5; SEQ ID NO: 6.

In another embodiment of the second aspect of the invention, the peptide consists of a sequence selected from the group consisting of: SEQ ID NO: 1; SEQ ID NO: 2; SEQ ID NO: 3; SEQ ID NO: 4; SEQ ID NO: 5; SEQ ID NO: 6. In another embodiment of the second aspect of the invention, the peptide of the first aspect of the invention is selected from the group consisting of: sequence SEQ ID NO: 1, SEQ ID NO: 2; SEQ ID NO: 3; SEQ ID NO: 4; SEQ ID NO: 5 or SEQ ID NO: 6.

In a third aspect the present invention provides a nucleotide sequence coding a peptide as defined in the first aspect of the invention or a fusion protein as defined in the second aspect of the invention.

There are well-known techniques in the state of the art for obtaining the nucleotide sequence from an amino acid sequence. When doing such sequencing it is of particular relevance the cell wherein the expression will take place. As it is well-known, the genetic code is degenerate, so there can be more than one nucleotide sequence coding for the same amino acid sequence. The use of codons varies depending on the host cell in terms of expression efficiency. The nucleotide sequence may in principle be optimized for increased expression depending on the host cell. As it is explained below, the nucleotide sequence coding for peptide sequence SEQ ID NO:1 has been optimized for expression in *M. pneumoniae*.

In one embodiment of the third aspect of the invention, the peptide of the first aspect of the invention is coded by a nucleotide sequence comprising a sequence having at least 90% of homology with one of the sequences of the group consisting of: SEQ ID NO: 7 to SEQ ID NO: 11:

SEQ ID NO: 7
ATGAAGTCCAAGTTGAAACTCAAACGCTATTTACTCTTTCTCCCCTTGTT

ACCACTCGGTACCTTGAGTTTAGCTAACACTTAC

SEQ ID NO: 8
ATGAAATCGAAGCTAAAGTTAAAACGTTATTTACTGTTTTTACCACTTTT

ACCGCTAGGGACGTTGTCACTAGCCAACACCTAC

SEQ ID NO: 9
ATGAAACTGAAACTTAAATTTCTATTAATTTCTCTTTTAGGTTCTAGTTT

GTTGTTAAGCGCTTGTTCTTCAGCAGCTACTCAA

SEQ ID NO: 10
ATGAAATTTAAGTATGGTGCCATTGTTTTCAGTGGTCTTTTAGGAGTCTC

TGCCATTTTAGCTGCTTGTGGTACA

SEQ ID NO: 11
ATGAAGCTTAGTGCTATTATCTCCCTATCAGTCGCTGGTACTGTGGGAAC

AACTGCGGTGGTAGTACCTACAACTATAACGCTTGTAAATAAG

In another embodiment of the third aspect of the invention, the peptide of the first aspect of the invention is coded by a nucleotide sequence comprising a sequence having at least 90% of identity with one of the sequences of the group consisting of: SEQ ID NO. 7 to SEQ ID NO: 11. In another embodiment of the third aspect of the invention, the peptide of the first aspect of the invention is coded by a nucleotide sequence consisting of a sequence having at least 90% of homology with one of the sequences of the group consisting of: SEQ ID NO. 7 to SEQ ID NO: 11. In another embodiment of the third aspect of the invention, the peptide of the first aspect of the invention is coded by a nucleotide sequence consisting a sequence having at least 90% of identity with one of the sequences of the group consisting of: SEQ ID NO. 7 to SEQ ID NO: 11. In another embodiment the peptide is coded by a nucleotide sequence consisting of a sequence selected from the group consisting of SEQ ID NO: 7 to SEQ ID NO: 11.

In another embodiment, the nucleotide sequence of the third aspect of the invention is operably linked to a promoter.

The term "operably linked to a promoter" as used herein refers to a functional linkage between the promoter sequence and the sequence coding for a fusion protein of the invention. This functional linkage is performed through the fusion of a DNA sequence corresponding to any *Mycoplasma pneumoniae* promoter, or a promoter from other bacteria compatible with *M. pneumoniae*, or a designed promoter capable of driving expression in *M. pneumoniae*, with the DNA sequence of the fusion protein (secretion peptide+POI) as is evident to any skilled person in the art. In principle the distance between the beginning of transcription after the promoter and the initial Methionine codon of the secretion signal should be less than 100 bases and preferably less than 50 bases. The promoter sequence initiates and mediates transcription of the DNA corresponding to the fusion protein coding sequence.

The selection of the promoter is made in view of the particular host cell and also in view of different variables involved in the production of the desired protein, such as inducible or constitutive expression, for instance. The skilled person in the art, using the general knowledge, is able of selecting the more appropriate promoter.

In another embodiment, the nucleotide sequence of the third aspect of the invention is operably linked to a promoter, the promoter typically being located upstream of the transcription start codon.

In still another embodiment, the nucleotide sequence of the third aspect of the invention is operably linked to an EfTu promoter. As it is shown below, EfTu promoter has been revealed by the experimental results to give high expression efficiency when the host cell is *M. pneumoniae*.

EfTu promoter sequence is available in several databases, The sequence used in the present invention is SEQ ID NO: 12:

GAAGACCTTTTGTGCTAACGCCAGTTTGGCAAATCAAGTTCTGATTTTGC

AATTATTTTGCTCCATATGAATTACACTACTCCAAGAATTATAAGCCTCT

CTACAGCTTTATCTCAAACTTATGTAAAATTAGAGACGTAATTCAAACAC

In still another embodiment, the nucleotide sequence of the third aspect of the invention is operably linked to EfTu promoter, which is upstream of the transcription start codon.

In a fourth aspect the present invention provides a vector comprising the nucleotide sequence of the third aspect of the invention coding for the fusion protein.

The incorporation of the nucleotide sequence of the third aspect of the invention in the vector is performed via any of the routine protocols Known to anyone skilled in the field of molecular biology.

In one embodiment of the fourth aspect of the invention, the vector is of the minitransposon Tn4001 type (Chopra-Dewasthali, R., et al. "First steps towards the genetic manipulation of *Mycoplasma agalactiae* and *Mycoplasma bovis* using the transposon Tn4001 mod" Int. J. Med. Microb. 2005, vol. 294, pp. 447-453)

In one embodiment of the fourth aspect of the invention, the vector is of the mini-Tn4001PsPuro (GenBank accession no. FJ872396).

In another embodiment of the fourth aspect of the invention, the vector is of minitransposon Tn4001PsPuro type and the nucleotide sequence is one comprising (a) a sequence having at least a 90% of homology with a sequence of the group consisting of: SEQ ID NO 7 to SEQ ID NO: 11, and (b) a sequence coding for the POI. In another embodiment of the fourth aspect of the invention, the vector is of the same type as cited above, and the nucleotide sequence is one comprising (a) a sequence having at least a 90% of identity with a sequence of the group consisting of: SEQ ID NO 7 to SEQ ID NO: 11, and (b) a sequence coding for the POI.

In another embodiment of the fourth aspect of the invention, the vector is of the minitransposon Tn4001PsPuro type and the nucleotide sequence is one comprising (a) a sequence having at least a 90% of homology with a sequence of the group consisting of: SEQ ID NO 7 to SEQ ID NO: 11, (b) a sequence coding for the POI(s); and (c) EfTu promoter located upstream of the transcription start codon. In another embodiment of the fourth aspect of the invention, the vector is of the same type as cited above and the nucleotide sequence is one comprising (a) a sequence having at least a 90% of identity with a sequence of the group consisting of: SEQ ID NO 7 to SEQ ID NO: 11, (b) a sequence coding for the POI(s); and (c) EfTu promoter located upstream of the transcription start codon.

In another embodiment of the fourth aspect of the invention, the vector is of minitransposon Tn4001PsPuro type and the nucleotide sequence is one comprising (a) a sequence having at least a 90% of homology with a sequence of the group consisting of: SEQ ID NO 7 to SEQ ID NO: 11, and (b) a sequence coding for the POI. In another embodiment of the fourth aspect of the invention, the vector is of the minitransposon Tn4001PsPuro type and the nucleotide sequence is one comprising (a) a sequence having at least a 90% of identity with a sequence of the group consisting of: SEQ ID NO 7 to SEQ ID NO: 11, and (b) a sequence coding for the POI.

In another embodiment of the fourth aspect of the invention, the vector is of minitransposon Tn4001PsPuro type and the nucleotide sequence is one comprising (a) a sequence having at least a 90% of homology with a sequence of the group consisting of: SEQ ID NO 7 to SEQ ID NO: 11, (b) a sequence coding for the POI(s); and (c) EfTu promoter located upstream of the transcription start codon. In another embodiment of the fourth aspect of the invention, the vector is of the minitransposon Tn4001PsPuro type and the nucleotide sequence is one comprising (a) a sequence having at least a 90% of identity with a sequence of the group consisting of: SEQ ID NO 7 to SEQ ID NO: 11, (b) a sequence coding for the POI(s); and (c) EfTu promoter located upstream of the transcription start codon.

In other embodiment of the fourth aspect of the invention, the vector comprises other regulatory elements for improving the expression of the fusion protein, such as ribosomal binding sites, transcription start and termination sequences, translation initiation sites, co-expression of other polypeptides that can be used for later selection of clones (reporter genes). The vector can for instance be constructed in such a way as to allow the controlled production of the fusion protein under specific circumstances, such as for instance the presence or absence of an inductor.

In another aspect, the present invention provides a host cell comprising the fusion protein of the second aspect of the invention or the vector of the fourth aspect of the invention.

The term "host cell" as used herein is a prokaryotic cell that has been genetically engineered so that it expresses the fusion protein of the invention. In a particular embodiment, the "host cell" is a prokaryotic cell into which one or more vectors or isolated and purified nucleic acid sequences of the invention have been introduced. It is understood that it refers not only to the particular subject cell but also to the progeny or potential progeny of such a cell. Because certain modifications may occur in succeeding generations due to either mutations or environmental influences, such progeny may not, in fact, be identical to the parent cell, but are still included within the scope of the term as used herein.

The host cell of the invention can be used as a "factory" of the POI of interested, being cultured in vitro under adequate conditions (the conditions will depend on the specific cell). In this embodiment, the cell is grown in an appropriate medium under adequate conditions and it will start the expression of the fusion protein, ie. the POI fused to the peptide. Thanks to the signal peptide of the invention, the POI will be efficiently exported through the membrane.

Alternatively, if selected host cell is intended to be administered to a human being or non-human animal as therapeutic tool in such a way that POI is produced in situ, and it is either unsafe or toxic, the selected host cell has to be engineered previous to its transformation with the vector of the present invention in order to develop a safe non-toxic host cell.

In a further aspect the present invention provides a pharmaceutical or veterinary composition.

The term "pharmaceutically or veterinary acceptable" refers to excipients or carriers to be used in pharmaceutical or veterinary technology, for preparing compositions for medical use, either in human beings or animals. Each one of the components has to be acceptable from the pharmaceutical or veterinary point of view, having to be compatible with the other ingredients of the pharmaceutical or veterinary composition. It has to be also for use in contact with tissue or human or animal organs without giving rise to excessive toxicity, irritation, allergic response, immunogenicity or other problems or side-effects. The expression "therapeutically effective amount" as used within the context of the present invention, refers to the amount of a compound or a host cell that, when administered, is sufficient to prevent development of, or alleviate to some extent, one or more of the symptoms of the disease which is addressed. The particular dose administered according to this invention will of course be determined by the particular circumstances surrounding the case, including the host cell administered, the fusion protein that it produces, the route of administration, the particular condition being treated, and similar considerations.

The fusion protein of the second aspect of the invention can for instance be used for a variety of therapeutic applications. If the POI is a foreign protein antigen, the fusion protein can be used for eliciting an immune response against it, as long as the presence of the peptide signal (secretion enhancer) does not alter its structure and function. Alternatively, if the POI is a therapeutic protein known to have a beneficial effect, the fusion protein can be used in the treatment of disease.

In a particular embodiment, the host cell is a bacterial host cell. In another embodiment, the host cell is an infectious bacteria. In another particular embodiment of the fifth aspect of the invention, the bacterial host cell belongs to the genus *Mycoplasma*. In another particular embodiment of the fifth aspect of the invention, the bacterial host cell is *Mycoplasma pneumoniae*. In another embodiment, it is a safe non-toxic host cell, either of wild-type or engineered. In another embodiment, it is a safe non-toxic engineered host cell. In another embodiment, it is a safe non-toxic engineered bacterial host cell.

*M. pneumoniae* is an ideal starting point for designing a minimal cell for use as bacterial therapy chassis. It has a small (860 kb) and comprehensively annotated genome, and a rich collection of functional genomic data describing its transcriptome, methylome, proteome, and metabolome. A flux balance model describing its metabolism is also available. In addition, it is closely related to *M. genitalium* and *M. mycoides* whose genomes have been chemically synthesized, transplanted, and comprehensively modelled. Furthermore, *M. pneumoniae* is well-suited for bacterial therapy because it is a weak human lung pathogen, divides very slowly (8-20 h), there are non-pathogenic strains, it does not have a lipolisacharide envelope (LPS) and is easily treated with commercially available antibiotics.

As it has been stated above, the fusion protein of the second aspect retains POI's function. When POI is a therapeutic polypeptide, the fusion protein or even the host cell of the fifth aspect of the invention can be used in therapy.

The host cell of the fifth aspect of the invention can be formulated in such a way as to improve its administration into different tissues.

In a particular embodiment of the seventh aspect of the invention, the fusion protein or the host cell is for use in the treatment of pulmonary disease.

The former two embodiments can be reformulated into a method of treatment of a disease comprising the administration of the fusion protein of the second aspect of the invention or the host cell of the fifth aspect of the invention in a therapeutically effective amount to a subject in need thereof, and to a method of treatment of a pulmonary disease comprising the administration of the fusion protein of the second aspect of the invention or the host cell of the fifth aspect of the invention in a therapeutically effective amount to a subject in need thereof, respectively.

Furthermore, the transformed bacteria could also be used for the dispersion of bacterial biofilms. As it is well-known, bacteria are capable of sticking to surfaces with the help of a biofilm. That is, they produce and secrete a number of extracellular polymeric substances (basically proteins and polysaccharides) that form a matrix that allows them to colonize both organic and inorganic substrates. This matrix not only serves as a fixation means, but also acts as a barrier often effectively turning the bacteria into antibiotic resistant. It can be devised that the host cells of the present invention could find both therapeutic and non-therapeutic uses related to the destruction of bacterial biofilms. The peptides of the present invention can be fused to a series of hydrolysing enzymes capable of breaking down the polysaccharide matrix. These fusion proteins can find both therapeutic and non-therapeutic applications. Therefore, it is also part of the invention:

(i) the host cell of the fifth aspect for use in the degradation of a bacterial biofilm. This applies for instance, to cystic fibrosis or any other pulmonary disease that involves biofilm formation.
(ii) the use of the host cell of the fifth aspect of the invention for the degradation of bacterial biofilms (for example to clean medical devices like caterers where biofilms could be found).

Throughout the description and claims the word "comprise" and variations of the word, are not intended to exclude other technical features, additives, components, or steps. Furthermore, the word "comprise" and its variations encompasses the term "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

A) Material and Methods

To produce and secrete therapeutic proteins, inventors analysed the secretome of *M. pneumoniae*. Then, they used this knowledge to build a series of vectors to produce and secrete recombinant therapeutic proteins in *M. pneumoniae*. Normal *M. pneumoniae* media is rich in proteins which interfere with MS analysis. Therefore inventors used the minimal media of *M. pneumoniae* as basic growth media for our experiment (Yus, E. et al. "Impact dof genome reduction on bacterial metabolism and its regulation", Science 2009, vol. 326, pp. 1263-1268) and replaced bovine serum albumin (BSA) as lipid carrier with (2-hydroxy)propyl-β-cyclodextrin (Hyprop).

After growing *M. pneumoniae* cells during 24 h and 72 h the supernatant media was harvested and ratios of intracellular to extracellular protein concentrations were obtained by dimethyl labelling and mass spectroscopy analysis. On average inventors obtained ratios for 281 out of 688 proteins from *M. pneumoniae* per experiment.

The proteins with highest extracellular to intracellular ratios were further analysed by the algorithm Signal P 3.0. Based on the predicted secretion signals inventors designed 11 vectors comprising a promoter and a secretion signal fused to the therapeutic proteins. As negative control inventors fused the 50 N-terminal residues of a cytosolic protein (Mpn332) to the therapeutic proteins. As promoter inventors chose either the promoter corresponding to the coding sequence of the secretion signal or if it was part of an operon with a distal promoter inventors put it under the control of the EfTu promoter. A detailed list of all constructs made, indicating the signal peptide and promoters can be found In Tables 1-3 found below for Alginate lyase, p53 and A1AT.

TABLE 1

Secretion constructs and strains with alginate lyase A1-III

| Name strain | Signal peptide | Signal Type | Promoter | Promoter Length [Bp] | Signal length [AA] | Cargo |
|---|---|---|---|---|---|---|
| Mpn142(Opt)-A1-III | Mpn142(Opt) | SpI | EfTu | 150 | 31 AA | A1-III |
| Mpn142-A1-III | Mpn142 | SpI | EfTu | 150 | 31 AA | A1-III |
| Mpn152-A1-III | Mpn152 | SpII | Mpn152 | 106 | 33 AA | A1-III |
| Mpn200-A1-III | Mpn200 | SpII | Mpn200 | 197 | 28 AA | A1-III |
| Mpn213-A1-III | Mpn213 | SpI | EfTu | 150 | 34 AA | A1-III |
| Mpn332-A1-III | Mpn332 | Neg control | EfTu | 150 | 50 AA | A1-III |
| Mpn400-A1-III | Mpn400 | SpI | Mpn400 | 160 | 41 AA | A1-III |
| Mpn489-A1-III | Mpn489 | SpII | Mpn489 | 100 | 34 AA | A1-III |
| Mpn506-A1-III | Mpn506 | SpII | Mpn506 | 117 | 28 AA | A1-III |
| Mpn588-A1-III | Mpn588 | SpI | Mpn588 | 100 | 30 AA | A1-III |
| Mpn592-A1-III | Mpn592 | SpII | Mpn592 | 100 | 36 AA | A1-III |
| Mpn645-A1-III | Mpn645 | SpII | EfTu | 150 | 31 AA | A1-III |

TABLE 2

Secretion constructs and strain with A1AT

| Name strain | Signal peptide | Signal Type | Promoter | Promoter length [Bp] | Signal length [AA] | Cargo |
|---|---|---|---|---|---|---|
| Mpn142(Opt)-A1AT | Mpn142(Opt) | SpI | EfTu | 150 Bp | 31 AA | A1AT |
| Mpn142-A1AT | Mpn142 | SpI | EfTu | 150 Bp | 31 AA | A1AT |
| Mpn200-A1AT | Mpn200 | SpII | Mpn200 | 197 Bp | 28 AA | A1AT |
| Mpn332-A1AT | Mpn332 | Neg control | EfTu | 150 Bp | 50 AA | A1AT |
| Mpn400-A1AT | Mpn400 | SpI | Mpn400 | 160 Bp | 41 AA | A1AT |
| Mpn489-A1AT | Mpn489 | SpII | Mpn489 | 100 Bp | 34 AA | A1AT |
| Mpn506-A1AT | Mpn506 | SpII | Mpn506 | 117 Bp | 28 AA | A1AT |
| Mpn645-A1AT | Mpn645 | SpII | EfTu | 150 Bp | 31 AA | A1AT |

TABLE 3

Secretion constructs and strain with p53

| Name strain | Signal peptide | Signal Type | Promoter | Promoter Length [Bp] | Signal length [AA] | Cargo |
|---|---|---|---|---|---|---|
| MPN142-p53 | Mpn142 | SpI | EfTu | 150 | 31 AA | p53 |
| MPN200-p53 | Mpn200 | SpII | Mpn200 | 197 | 28 AA | p53 |
| Mpn332-p53 | Mpn332 | Neg control | EfTu | 150 | 50 AA | p53 |
| MPN400-p53 | Mpn400 | SpI | Mpn400 | 160 | 41 AA | p53 |
| MPN489-p53 | Mpn489 | SpII | Mpn489 | 100 | 34 AA | p53 |
| MPN506-p53 | Mpn506 | SpII | Mpn506 | 117 | 28 AA | p53 |
| MPN459-p53 | Mpn459 | SpI | EfTu | 150 | 57 AA | p53 |
| MPN645-p53 | Mpn645 | SpII | EfTu | 150 | 31 AA | p53 |

The tables also indicate whether the secretion signals are predicted to belong to membrane anchored lipoproteins (SpII) or sec mediated secreted proteins (SpI).

Inventors cloned the three therapeutic proteins fused to the secretion peptide and the respective promoter in a miniTn4001-Puro-1 vector (GenBank accession number: KC816623). The constructs were assembled and scaled up in E. coli before transformation in M. pneumoniae. Inventors determined the levels of the secreted protein either by an activity assay for the alginate lyase constructs or by ELISA measurements for A1AT and p53. In all cases, the constructs under the control of the EfTu promoter showed the highest level of secreted protein, while no signal was detected for the negative control.

Inventors designed a battery of sequences that when fused to heterologous proteins result in their efficient expression and secretion. To validate the vector sequences, inventors selected three different proteins having possible therapeutic applications and different biochemical and folding properties: an enzyme exemplified by poly M Alginate lyase A1-III (alginase), an oligomeric protein: p53 (which folds as a tetramer) and a protein with a difficult fold:□1-antitrypsin (A1AT).

Bacterial Strains and Growth Conditions

For constructing DNA vectors and secretion constructs different E. coli strains were used. Mainly Top10 (life technologies), Stbl4 (life technologies) or copy cutter cells (epicentre). The cells were grown at 30° C.-37° C. in LB or 2×TY medium with 100 ug/ml of Ampiciline for selection.

M. pneumoniae M129 strain was grown in T150 flasks at 37° C. in modified Hayflick medium as previously described (Yus, E., et al. ibid). When selecting for Puromycin resistance 3 µg/ml were used. For the proteomics studies of the secreted proteins the cells were grown in modified minimal media. To make the minimal media compatible with MS analysis the lipid carrier BSA was exchanged to 5 mM cyclodextrin Hydroxypropyl of estimated mol weight 1396Da (Sigma H107).

Experimental Determination of the Secretome

M. pneumoniae is usually cultured in modified Hayflick media, a rich media containing many proteins from added horse serum. The highly abundant proteins from the rich media cover the signal from low abundant secreted proteins leaving them unsuitable for mass spectrometric (MS) analysis.

Therefore, inventors used the minimal media of M. pneumoniae as growth media for our experiment (Yus et al., ibid). This minimal media still contains bovine serum albumin (BSA) as lipid carrier in high amounts. Inventors replaced BSA with 5 mM (2-hydroxy)propyl-β-cyclodextrin (Hyprop) (Sigma H107 CAS Number 128446-35-5) (Greenberg-Ofrath et al., "Cyclodextrins as carriers of cholesterol and fatty acids in cultivation of mycoplasmas" Appl. Environ. Microbiol. 1993, vol. 59, pp. 547-551) and could so obtain a protein free Media compatible with downstream MS analysis.

To produce our supernatants inventors grew wt M129 in normal media for 3 days. Before splitting the cultures were washed twice with PBS while attached and twice after scraping. Inventors then split it 1:10 in a 150 cm2 flask containing 40 ml of Hyprop media. Inventors started at each repeat of the experiment two flask one for each time point. The cells were allowed to attach for 24 h and were the attached cells were washed twice again with PBS to remove all trace amounts from the horse serum. Inventors then let the cells grow another 72 h before removing the supernatant and harvesting the cells of the first flask. The attached cells were resuspended in exactly the same amount of Hyprop media as the removed supernatant. In the other flask only the supernatant was removed and the attached cells were washed twice with PBS before 35 ml of fresh media was added. After 24 h this flask was harvested as the first one.

The cell suspension was always processed identical and in parallel to the supernatants to avoid any bias from experimental procedure on the outcome. The samples were precipitated with 60% acetone (Sigma product #179124) and 10% trichloracetic acid (TCA) (Sigma product # T9159) as final concentration. The mixture was spun for 1 h at 35000 g (4° C.). The supernatant was discarded and the pellets resuspended in 1.5 ml of TCA/acetone and spun 2 h at 16000 g (4° C.). The supernatant was removed and the pellet was dried completely in a speed vac before being redisolved in a buffer of 8 M Urea and 100 mM NaHCO3 using a bioruptor system. The total protein amounts in the samples were determined using BCA assay (Pierce product # 23225). The UPF-CRG Proteomics facility then normalised, digested and labelled the samples. Inventors used dimethyl labelling to label the different samples. Three Labels were used heavy, medium and light. Equal amounts of the samples mixed and analysed by nano LC/MS/MS to obtain ratios of intracellular to extracellular protein concentrations as previously described (Boersema et al., "Multiplex peptide stable isotope dimethyl labelling for quantitative proteomics" Nat. Protoc. 2009, vol. 4, pp. 484-494). Inventors calculated the p-Value of a bimodal distribution by standard methods. Inventors chose a conservative p-value of 0.001 as threshold to define a protein as secreted.

Molecular Biology Methods

All constructs were cloned in mini-Tn4001-Puro vector (GenBank accession number: KC816623). First, inventors generated a set of vectors containing the secretion signals and promoters. All fragments comprising different secretion signals and promoters were amplified by PCR from *M. pneumoniae* genomic DNA. For the secretion signals carrying their own promoter inventors introduced the PstI and EcoRI sites for restriction cloning during the PCR and cloned the fragment by fast ligation. In the cases when the secretion signal had no own promoter and the EfTu promoter was used, inventors generated the constructs by the isothermal assembly method. Overhangs of 20 bp needed for the assembly were introduced by PCR. Detailed sequences of primers used are listed in Table 4, found below:

TABLE 4

| Name | Sequence |
|---|---|
| Mpn152 Rev | GTGTGCCTGCAGGCTgCCATCAACTTGGTTAAATTTGCCCCTTGCC |
| Mpn152 fwd | AAGCTTGATATCGAATTCGCTTTTAAAAATACTTTTACTTCAGTAACTCAAAC |
| Mpn200 Sig F | AAGCTTGATATCGAATTCGACAGTAGTTTAAACTGATTCTTTACCTC |
| Mpn200 Sig R | GTGTGCCTGCAGGCTgCCTTTACCGCGTGTACCACAAG |
| Mpn400 Sig F | AAGCTTGATATCGAATTCGCGTAAATTTTCTCCTTTAGGGATACT |
| Mpn400 Sig R | GTGTGCCTGCAGGCTgCCATTAACGATAGAACTGCGGAAAAAGCA |
| Mpn489 Sig F | AAGCTTGATATCGAATTCTTCACCTTCACCTATTTTATTAGC |
| Mpn489 Sig R | GTGTGCCTGCAGGCTgCCATTGGAGGTATTGAGTGC |
| Mpn506 Sig F | AAGCTTGATATCGAATTCGATTAAATTTTCATCTTAAAAGCTTTTATTTTTACC |
| Mpn506 Sig R | GTGTGCCTGCAGGCTgCCTTTACCCTTTGTACCACAGGCAGC |
| Mpn588 Sig F | AAGCTTGATATCGAATTCTTCAATTAATCATTGATGGTTTAAGTGTCTC |
| Mpn588 Sig R | GTGTGCCTGCAGGCTgCCAAAGTTTGGCTGGGTTGCCAG |
| Mpn592 Sig F | AAGCTTGATATCGAATTCAACAGACCTTTAGAAGAAGTGCGA |
| Mpn592 Sig R | GTGTGCCTGCAGGCTgCCATTTTTGTGATTAGTGTTAGCTACTGTTAGCGT |
| Mpn142 only signal_No1 | TAGAGACGTAATTCAAACACATGAAATCGAAGCTAAAGTTAAAACGTTATTTACTGTTTT |
| Mpn142 only signal_No2 | TGTTGGCTAGTGACAACGTCCCTAGCGGTAAAAGTGGTAAAAACAGTAAATAACGTTTTA |
| Mpn142 only signal_No3 | GACGTTGTCACTAGCCAACACCTACCTCCTCCAAGGcAGCCTGCAGCCCGGGGGGCAAGA |
| Mpn645 only signal_No2 | GTAGCTGCTGAAGAACAAGCGCTTAACAACAAACTAGAACCTAAAAGAGAAATTAATAGAA |
| Mpn645 only signal_No3 | CGCTTGTTCTTCAGCAGCTACTCAAGTAATTTCTGGcAGCCTGCAGCCCGGGGGGCAAGA |
| Mpn645 only signal_No1 | TAGAGACGTAATTCAAACACATGAAACTGAAACTTAAATTTCTATTAATTTCTCTTTTAG |
| eFTu Fwd | AAGCTTGATATCGAATTCGAAGACCTTTTGTGCTAACGCCAG |

TABLE 4-continued

| Name | Sequence |
| --- | --- |
| eFTu Rev | GTTTTGAATTACGTCTCTAATTTTACATAAGTTTG |
| Mpn459 F | GACGTAATTCAAACACATGGCTTTCATGCCATGTTTTTCATATAGC |
| Mpn459 Rev | GTGTGCCTGCAGGCTgCCAGTAACATAAACATCTCGTGCTTGGGC |
| Mpn213 Rev | GTGTGCCTGCAGGCTgCCTTGGTGGGCTTATTTACAAGCGTTATAGTTGTAGG |
| Mpn213 F | GACGTAATTCAAACACATGAAGCTTAGTGCTATTATCTCCCTATCAGTCG |
| Mpn332 | ATGCCAGCTGTAAAAA |
| Mpn332 | GACTAACACCAAACGTTT |

Mpn152 Rev, SEQ ID NO: 13; Mpn 152 fwd, SEQ ID NO: 14; Mpn200 Sig F, SEQ ID NO: 15; Mpn200 Sig R, SEQ ID NO: 16; Mpn400 Sig F, SEQ ID NO: 17; Mpn400 Sig R, SEQ ID NO: 18; Mpn489 Sig F, SEQ ID NO: 19; Mpn489 Sig R, SEQ ID NO: 20; Mpn506 Sig F, SEQ ID NO: 21; Mpn506 Sig R, SEQ ID NO: 22; Mpn588 Sig F, SEQ ID NO: 23; Mpn588 Sig R, SEQ ID NO: 24; Mpn592 Sig F, SEQ ID NO: 25; Mpn592 Sig R, SEQ ID NO: 26; Mpn 142 only signal_No1, SEQ ID NO: 27; Mpn142 only signal_No2, SEQ ID NO: 28; Mpn142 only signal_No3, SEQ ID NO: 29; Mpn645 only signal_No2, SEQ ID NO: 30; Mpn645 only signal_No3, SEQ ID NO: 31; Mpn645 only signal_No1, SEQ ID NO: 32; eFTu Fwd, SEQ ID NO: 33; eFTu Rev, SEQ ID NO 34; Mpn459 F, SEQ ID NO: 35; Mpn459 Rev, SEQ ID NO: 36; Mpn213 Rev, SEQ ID NO: 37; Mpn213 F, SEQ ID NO: 38; Mpn332, SEQ ID NO: 39; Mpn332, SEQ ID NO: 40.

The resulting vectors derived from mini-Tn4001-Puro vector were linearized using the restriction enzymes EcoRI (NEB R0101) and PstI-Hf (NEB R3140) and subsequently dephosphorylated using Antartic phosphatse (NEB M0289). The different therapeutic proteins were synthetized and cloned into the EcoRI and PstI-Hf digested vectors.

Mpn142 Opt (Design and Cloning)

The secretion signal of Mpn142 (First 93 coding bp) was ordered from DNA 2.0, the company changed the codon choice to reduce secondary structure in the region of the secretion signal. Inventors then cloned this sequence as fusion to the target proteins. For the cloning inventors used Gibson cloning and eliminated the previously used PstI restriction site.

Several publications showed that the secondary structure at the 5' end of an mRNA influences the transcriptional efficiency. Recently, it has been shown that this effect is emphasized on mRNA without a clearly defined RBS site. Most transcripts of M. pneumoniae lack an RBS site and all constructs for production and secretion of alginate lyase were designed without RBS site. Inventors therefore hypothesized that a reduction of mRNA secondary structure in the secretion signal could improve the translational efficiency.

Expression and Assessment of Activity in Different Proteins.

Neutrophil Elastase Activity Assay.

Inventors measured the activity of A1AT indirectly through the inhibition of neutrophil elastase. The activity of neutrophil elastase was measured either by a colorimetric or fluorescence based assay. For this the commercially available substrate N-Methoxysuccinyl-Ala-Ala-Pro-Val p-nitroanilide (Sigma product # M4765) or the cleavage of a quenched fluorescence substrate N-Methoxysuccinyl-Ala-Ala-Pro-Val-AMC (Merck millipore product #324740) was used. The reaction buffer is 0.1 M Tris ph 7.5. In the colorimetric assay the release of free 4-nitroaniline was followed at 400 nm and in the fluorescence assay an excitation of 370 nm was used and the emission was recorded at 445 nm.

Enrichment of A1AT for Neutrophil Elastase Activity Measurements

To measure concentrated minimal media supernatant, inventors first improved the culture condition to reduce the carryover of horse A1AT originating in the pre culture to a minimum. Inventors grew a pre-culture in full Hayflick medium, the media was aspirated and cells were washed twice with PBS. Then, the cells were scraped and split 1:10 in minimal media. The minimal media was aspirated and replaced with fresh media after 24 h. The culture was grown for 48 and then the supernatant was harvested. To measure A1AT activity on concentrated media 200 µl of supernatant were reduced to a volume of 20 µl using an Amicon ultrafiltration device with a 30 kDa cut-off and then the A1AT activity was tested.

To enrich A1AT by affinity chromatography inventors used the Strep-TagII fused to A1AT. Inventors harvested supernatant from 300 cm2 culture dish with cells grown in full Hayflick media. The media was run over a 1 ml StrepTrap HP column (GE Healthcare product #28-9075-46). The column was then washed with 6 column volumes of wash buffer (100 mM Tris, pH 8.0, 150 mM NaCl, 1 mM EDTA) and subsequently eluted with wash buffer supplemented with 2.5 mM desthiobiotin. The concentration of A1AT was determined by ELISA.

P53 and A1AT Quantification by ELISA

Inventors used commercially available Kits for the quantification of human A1AT (USCN Product No.: SEB697Hu) and a p53 pan ELISA (Roche Product No.: 11828789001). For the assay inventors followed the manufacturer's instructions.

Alginate Lyase Assay

To measure alginate lyase activity in full media the assay developed by Kitamikado, M., et al. "Method designed to detect alginate-degrading bacteria" Appl. Environ. Microbiol. 1990, vol, 56, pp. 2939-2940) was used. Briefly, 0.1% of alginate substrate is added to the media and with the cells. At various time points 0.2 ml of media supernatant is put in a test tube and 2.0 ml of an acidic albumin solution (3.26 g sodium acetate, 4.56 ml of glacial acetic acid, 1.0 g of bovine albumin fraction V are filled up to 1l with water and ph adjusted to 3.75 with HCl). In the presence of polymeric alginate a white precipitate is formed. A small aliquot of the mixture is then transferred to a plate and the absorbance is measured.

Inventors tested different wavelengths for the signal to noise ratio and found 300 nm to be the most sensitive, while everything up to 660 nm gave good reliable readings.

B) Results

Overall, the results presented here are the proof of concept that *M. pneumoniae* can be used as a delivery system to express and secrete active proteins with a range of applications, including those related to therapy. They show that it is possible to engineer *M. pneumoniae* to produce and secrete therapeutic proteins. Inventors could produce and detect in the supernatant 3 different proteins, two of which are of human origin (p53/A1AT) and of which only two are normally secreted (alginate lyase/A1AT). Inventors could prove that our secretion vector worked reliably with the same construct yielding the highest yields for all three proteins. Further, we could show that two out of the three proteins are correctly folded and active after secretion.

Quantitative Analysis of the Secreted Proteins by *M. pneumoniae.*

Inventors designed 11 vectors comprising a promoter and a secretion signal fused to the three therapeutic proteins (A1AT, p53, Alginase). As a negative control inventors fused a fragment of the same length corresponding to the N-terminus of a cytosolic protein (Mpn332) to the three proteins.

Quantitative analysis of the secreted p53 by *M. pneumoniae* After transforming *M. pneumoniae* cells with each of the engineered p53 constructs, p53 secretion was verified by using a p53 pan sandwich ELISA (Roche). To assess the dynamics of p53 accumulation in the supernatant, the absolute concentrations of p53 in the media was measured at various time points after inoculation. Inventors characterized protein secretion both in modified Hayflick (Full Media) and McCoy media which is commonly used for mammalian cell culture. The results for secretion in McCoy media are summarized in FIG. 1. The constructs Mpn-142 and Mpn-645 under control of the Eftu promoter showed the highest concentration of p53 in the supernatant media. Interestingly the p53 concentration in the supernatant for most constructs peaked at 48 h when the cells enter into stationary phase and then slowly dropped again. This could either indicate either a regulation of secretion or gene expression which is linked to the switch from exponential to stationary phases of growth. Also, a balance between secretion and extracellular breakdown by proteases could explain this result.

Quantitative and Functional Analysis of the Secreted Alginate Lyase A1-III by *M. pneumoniae*

Inventors further analysed the secretion and activity of alginate lyase in *M. pneumoniae*. First the gene was cloned in our secretion constructs and then transformed into *M. pneumoniae*. To evaluate the secretion efficiency inventors used an assay for alginate lyase activity. As with the p53 constructs the two constructs with the alginate lyase under control of the EfTu promoter and with the secretion signals of Mpn-142 and Mpn-645 performed the best (FIG. 2). Both showed degradation of the alginate in the media already at day 1. While the majority of the constructs showed no sign of alginate degradation even after 5 days of incubation. The constructs with the secretion signals of Mpn-200 and Mpn-400 which are both under their respective promoter showed degradation of alginate at day 2 and the construct with the secretion signal of Mpn-489 and its respective promoter showed degradation only at day 5 after inoculation. The negative control which is fused to the 50 N-terminal amino acids of the cytosolic protein Mpn-332 showed no sign of degradation. No differences in growth rate of different *M. pneumoniae* strains were observed in comparison with wt indicating that the promoter activity is a determining factor for the production and secretion of alginate lyase.

In order to test if this system could be implemented in a less immunogenic strain, we tested whether the secretion constructs also work in a non-adherent strain. This strain lacks part of the adhesion and gliding machinery, main factors in virulence and pathogenicity. The results obtained in the non-adherent strain matched up with the results obtained in wt M129 strain implying that the same secretion vectors can be used in non-pathogenic strain.

In order to improve the levels of protein production, inventors designed a new Mpn-142 secretion signal (Mpn-142(Opt) (which corresponds to SEQ ID NO:7) with a minimized secondary structure in the 5' of the mRNA. The construct was still under the control of the EfTu promoter but the codons for the secretion signal were changed from the wt sequence following the recommendations of the company DNA 2.0. Inventors had observed earlier that *M. pneumoniae* grows better in Hayflick (full) media than in our modified minimal media used to characterize the secretome. To quantify the maximal amounts of alginate lyase produced by the different strains, inventors thus established a quantitative assay compatible with full media based on the previously used qualitative assay (Kitamikado et al., ibid). The absolute alginate lyase activity from the media of 2 strains was determined at different time points. The highest activity levels were observed for the Mpn-142(Opt) strain. In the media of the *M. pneumoniae* strain transformed with Mpn-142(Opt) inventors measured an activity corresponding to ~0.1 Units of alginate lyase. This corresponds to ~0.01 mg/ml of the alginate lyase (Sigma A1603) which we used as standard in our quantitative assay.

Inventors finally tested supernatants of the strains Mpn-142(Opt) and Mpn-142 in a *P. aeruginosa* biofilm assay. Inventors saw no anti biofilm activity while a positive control of media containing the same amount of alginate lyase activity, of a commercial alginate lyase (Sigma A1603) showed antibiofilm activity.

It has been reported that DNAse enhances the breakdown of *P. aeruginosa* biofilms. Based on this study inventors investigated whether *M. pneumoniae* M129 media supernatant contains Dnase activity that could already supply this function. For this propose, inventors measured lambda phage DNA degradation in the media from a M129 WT culture. After 1 h of incubation at 37° C. most of the DNA was digested indicating a strong Dnase activity in the supernatant of *M. pneumoniae* M129 wt supernatants. Only minor signs of degradation were observed in the control reaction corresponding to the media that had not been in contact with cells.

Quantitative analysis of the secreted A1AT by *M. pneumoniae* In order to test the activity of AA1T secreted by *M. pneumoniae*, first inventors measured the protein expression level in the supernatant for each strain using an ELISA kit from USCN. As shown in FIG. 3A a, secretion of AAT is better using full medium. The best secretion levels are obtained, as in the previous cases, from the Mpn-142 and Mpn-645 strains with a yield respectively of 250 ng/ml and 130 ng/ml using the full medium and 152 ng/ml and 20 ng/ml using the minimal medium after 73 h of culture. As with p53 inventors observed that the protein concentration in the supernatant peaked after 2-3 days and then decreased (FIG. 3*a*). Inventors tested whether the degradation of the secreted protein by an extracellular protease is the mechanism causing this peak. Therefore, inventors spiked supernatant of a wt M. pneumoniae culture grown either in minimal or full Hayflick media with 300 nM A1AT and incubated it for 96 h. Inventors measured the inhibitory effect on neutrophil elastase at different time points. All sample showed a constant maximal inhibition indicating no significant degradation in the supernatant over time. Inventors performed a similar test with BSA in supernatant and could also observe no proteolytic effect on a SDS Gel.

Then inventors analyzed if the secreted A1AT was functional. Unfortunately the full Hayflick media which yields the highest proteins concentrations also contains high level of Horse A1AT. This Horse A1AT interferes with functional neutrophil elastase assays while not showing up in the ELISA measurements The amounts of A1AT secreted in the minimal media is below the minimum concentration necessary for the functional assay 10 to 30 nM (500 ng/ml-1500 ng/ml) (FIG. 3A). To reach the concentration of 10 to 30 nM of AAT in the supernatant of Mpn-142 culture, inventors concentrated the samples from minimal media using ultrafiltration with an ultra-30K device (Amicon). As shown in FIG.3*b* concentrated supernatant showed a complete inhibition of NE activity compared to WT concentrated supernatant. However, inventors observed a decrease of NE activity in the minimal media alone in comparison with our control reaction in buffer only suggesting unspecific inhibition of NE activity following the volume reduction.

To further verify the activity of AAT secreted by *M. pneumoniae*, a purification process was performed. Inventors used a Strep Tag II which was introduced at C-terminus of the protein in conjunction with a Strep Tactin column to enrich the protein. The binding of the protein to the column was weak most likely because of the low concentration of A1AT in the media compared to the Kd of the Strep Tag II. Neither the less inventors could significantly enrich and purify the A1AT from the full media. Inventors then tested the purified protein in a Neutrophil elastase activity test and could show that the A1AT produced by *M. pneumoniae* is as active as A1AT produced by *E. coli* (FIG.3*c*).

After transforming *M. pneumoniae* cells with each of the engineered p53, A1AT and alginase constructs, inventors verified secretion in the supernatant in modified Hayflick (full media) at different time points using different analyses. In the case of p53 secretion was verified by using a p53 pan sandwich ELISA (Roche). In the case of the alginase, inventors checked the enzymatic activity (alginate degradation) in the supernatant. Finally, for A1AT inventors checked the expression in minimal media as well due to the abundance of horse A1At in the medium.

In the three cases, similar results were found (FIG. 1-FIG. 3) with the constructs Mpn-142 and Mpn-645 under the control of the EfTu promoter showing the highest concentration in the supernatant media. No differences in growth rate of different *M. pneumoniae* strains were observed in comparison with WT indicating that the promoter activity is a determining factor for the production and secretion of the proteins. These results indicate that the selected *P. pneumoniae* secretion signals worked similarly with very different proteins, and that: enzymes, oligomeric proteins or difficult folds can be effectively produced and released to the medium. For most constructs and cases the concentration in the supernatant in rich medium peaked at 48 h and then slowly dropped again. This could either indicate a regulation of secretion or gene expression which is linked to the switch from exponential to stationary phases of growth. Also, a balance between secretion and extracellular breakdown by proteases could explain this result.

Testing other strains and improving production.

In order to test if the secretion system could be implemented in a non-pathogenic strain, inventors tested whether the algynase constructs could also work in a non-adherent strain. This strain lacks part of the adhesion and gliding machinery, which are main factors in virulence and pathogenicity. The results obtained in the non-adherent strain matched up with the results obtained in M129 strain implying that the same secretion vectors can be used in non-pathogenic strains.

In order to improve the levels of protein production, inventors designed a new Mpn-142 secretion signal (Mpn-142(Opt)) with a minimized secondary structure in the 5' of the mRNA. The construct was still under the control of the EfTu promoter but the codons for the secretion signal were changed from the wt sequence. To quantify the maximal amounts of alginate lyase produced by the different strains, a quantitative assay compatible with full media based on a previously used qualitative assay was established. The absolute alginate lyase activity from the media of the MPN142 and MPN142(Opt) strains was determined at different time points. The highest activity levels were observed for the Mpn-142(Opt) strain in the media of the *M. pneumoniae* strain transformed with Mpn-142(Opt) inventors measured an activity corresponding to ~0.1 Units of alginate lyase. This corresponds to ~0.01 mg/ml of the alginate lyase (Sigma A1603) which was used as standard in the quantitative assay.

REFERENCES CITED IN THE APPLICATION

Chopra-Dewasthali, R., et al. "First steps towards the genetic manipulation of *Mycoplasma agalactiae* and *Mycoplasma bovis* using the transposon Tn4001 mod" Int. J. Med. Microb. 2005, vol. 294, pp. 447-453

Yus, E. et al. "Impact dof genome reduction on bacterial metabolism and its regulation", Science 2009, vol. 326, pp. 1263-1268

Greenberg-Ofrath et al., "Cyclodextrins as carriers of cholesterol and fatty acids in cultivation of mycoplasmas" Appl. Environ. Microbiol. 1993, vol. 59, pp. 547-551

Boersema et al., "Multiplex peptide stable isotope dimethyl labelling for quantitative proteomics" Nat. Protoc. 2009, vol. 4, pp. 484-494

Kitamikado, M., et al. "Method designed to detect alginate-degrading bacteria" Appl. Environ. Microbiol. 1990, vol, 56, pp. 2939-2940

The invention claimed is:

1. A nucleotide sequence encoding a peptide consisting of a sequence having at least 90% homology with, and having the same length as, a sequence selected from the group consisting of: SEQ ID NO: 1; SEQ ID NO: 2; SEQ ID NO: 3; SEQ ID NO: 4; SEQ ID NO: 5; and SEQ ID NO: 6, wherein said nucleotide sequence is operably linked to a heterologous promoter.

2. A vector comprising the nucleotide sequence of claim 1.

3. A host cell comprising the vector of claim 2, wherein the vector is heterologous to the host cell.

4. The host cell of claim 3, wherein the cell is a bacterial cell.

* * * * *

SEQUENCE LISTING

```
<160> NUMBER OF SEQ ID NOS: 40

<210> SEQ ID NO 1
<211> LENGTH: 28
<212> TYPE: PRT
```

-continued

```
<213> ORGANISM: Mycoplasma pneumoniae

<400> SEQUENCE: 1

Met Lys Ser Lys Leu Lys Leu Lys Arg Tyr Leu Leu Phe Leu Pro Leu
1               5                   10                  15

Leu Pro Leu Gly Thr Leu Ser Leu Ala Asn Thr Tyr
            20                  25

<210> SEQ ID NO 2
<211> LENGTH: 28
<212> TYPE: PRT
<213> ORGANISM: Mycoplasma pneumoniae

<400> SEQUENCE: 2

Met Lys Leu Lys Leu Lys Phe Leu Leu Ile Ser Leu Leu Gly Ser Ser
1               5                   10                  15

Leu Leu Leu Ser Ala Cys Ser Ser Ala Ala Thr Gln
            20                  25

<210> SEQ ID NO 3
<211> LENGTH: 38
<212> TYPE: PRT
<213> ORGANISM: Mycoplasma pneumoniae

<400> SEQUENCE: 3

Met Lys Leu Asn Phe Lys Ile Lys Asp Lys Lys Thr Leu Lys Arg Leu
1               5                   10                  15

Lys Lys Gly Gly Phe Trp Ala Leu Gly Leu Phe Gly Ala Ala Ile Asn
            20                  25                  30

Ala Phe Ser Ala Val Leu
            35

<210> SEQ ID NO 4
<211> LENGTH: 25
<212> TYPE: PRT
<213> ORGANISM: Mycoplasma pneumoniae

<400> SEQUENCE: 4

Met Lys Phe Lys Tyr Gly Ala Ile Val Phe Ser Gly Leu Leu Gly Val
1               5                   10                  15

Ser Ala Ile Leu Ala Ala Cys Gly Thr
            20                  25

<210> SEQ ID NO 5
<211> LENGTH: 31
<212> TYPE: PRT
<213> ORGANISM: Mycoplasma pneumoniae

<400> SEQUENCE: 5

Met Lys Leu Ser Ala Ile Ile Ser Leu Ser Val Ala Gly Thr Val Gly
1               5                   10                  15

Thr Thr Ala Val Val Val Pro Thr Thr Ile Thr Leu Val Asn Lys
            20                  25                  30

<210> SEQ ID NO 6
<211> LENGTH: 31
<212> TYPE: PRT
<213> ORGANISM: Mycoplasma pneumoniae

<400> SEQUENCE: 6

Met Gly Tyr Lys Leu Lys Arg Trp Pro Leu Val Ala Phe Thr Phe Thr
1               5                   10                  15
```

```
Gly Ile Gly Leu Gly Val Val Leu Ala Ala Cys Ser Ala Leu Asn
        20                  25                  30
```

<210> SEQ ID NO 7
<211> LENGTH: 84
<212> TYPE: DNA
<213> ORGANISM: Artificial Sequence
<220> FEATURE:
<223> OTHER INFORMATION: optimized sequence coding peptide Mpn142

<400> SEQUENCE: 7

```
atgaagtcca agttgaaact caaacgctat ttactctttc tccccttgtt accactcggt    60
accttgagtt tagctaacac ttac                                          84
```

<210> SEQ ID NO 8
<211> LENGTH: 84
<212> TYPE: DNA
<213> ORGANISM: Mycoplasma pneumoniae

<400> SEQUENCE: 8

```
atgaaatcga agctaaagtt aaaacgttat ttactgtttt taccactttt accgctaggg    60
acgttgtcac tagccaacac ctac                                          84
```

<210> SEQ ID NO 9
<211> LENGTH: 84
<212> TYPE: DNA
<213> ORGANISM: Mycoplasma pneumoniae

<400> SEQUENCE: 9

```
atgaaactga aacttaaatt tctattaatt tctcttttag gttctagttt gttgttaagc    60
gcttgttctt cagcagctac tcaa                                          84
```

<210> SEQ ID NO 10
<211> LENGTH: 75
<212> TYPE: DNA
<213> ORGANISM: Mycoplasma pneumoniae

<400> SEQUENCE: 10

```
atgaaattta agtatggtgc cattgttttc agtggtcttt taggagtctc tgccattta     60 gctgcttgtg gtaca                                                    75
```

<210> SEQ ID NO 11
<211> LENGTH: 93
<212> TYPE: DNA
<213> ORGANISM: Mycoplasma pneumoniae

<400> SEQUENCE: 11

```
atgaagctta gtgctattat ctccctatca gtcgctggta ctgtgggaac aactgcggtg    60
gtagtaccta caactataac gcttgtaaat aag                                93
```

<210> SEQ ID NO 12
<211> LENGTH: 150
<212> TYPE: DNA
<213> ORGANISM: Escherichia coli

<400> SEQUENCE: 12

```
gaagaccttt tgtgctaacg ccagtttggc aaatcaagtt ctgattttgc aattattttg    60
ctccatatga attacactac tccaagaatt ataagcctct ctacagcttt atctcaaact   120
tatgtaaaat tagagacgta attcaaacac                                   150
```

<210> SEQ ID NO 13
<211> LENGTH: 46
<212> TYPE: DNA
<213> ORGANISM: Artificial Sequence
<220> FEATURE:
<223> OTHER INFORMATION: Mpn152 Rev

<400> SEQUENCE: 13
gtgtgcctgc aggctgccat caacttggtt aaatttgccc cttgcc        46

<210> SEQ ID NO 14
<211> LENGTH: 53
<212> TYPE: DNA
<213> ORGANISM: Artificial Sequence
<220> FEATURE:
<223> OTHER INFORMATION: Mpn 152 fwd

<400> SEQUENCE: 14
aagcttgata tcgaattcgc ttttaaaaat acttttactt cagtaactca aac        53

<210> SEQ ID NO 15
<211> LENGTH: 47
<212> TYPE: DNA
<213> ORGANISM: Artificial Sequence
<220> FEATURE:
<223> OTHER INFORMATION: Mpn200 Sig F

<400> SEQUENCE: 15
aagcttgata tcgaattcga cagtagttta aactgattct ttacctc        47

<210> SEQ ID NO 16
<211> LENGTH: 38
<212> TYPE: DNA
<213> ORGANISM: Artificial Sequence
<220> FEATURE:
<223> OTHER INFORMATION: Mpn200 Sig R

<400> SEQUENCE: 16
gtgtgcctgc aggctgcctt taccgcgtgt accacaag        38

<210> SEQ ID NO 17
<211> LENGTH: 46
<212> TYPE: DNA
<213> ORGANISM: Artificial Sequence
<220> FEATURE:
<223> OTHER INFORMATION: Mpn400 Sig F

<400> SEQUENCE: 17
aagcttgata tcgaattcgc gtaaattttc tcctttaggg attact        46

<210> SEQ ID NO 18
<211> LENGTH: 46
<212> TYPE: DNA
<213> ORGANISM: Artificial Sequence
<220> FEATURE:
<223> OTHER INFORMATION: Mpn400 Sig R

<400> SEQUENCE: 18
gtgtgcctgc aggctgccat taacgattag aactgcggaa aaagca        46

<210> SEQ ID NO 19
<211> LENGTH: 42
<212> TYPE: DNA
<213> ORGANISM: Artificial Sequence
<220> FEATURE:

```
<223> OTHER INFORMATION: Mpn489 Sig F

<400> SEQUENCE: 19
aagcttgata tcgaattctt caccttcacc tattttatta gc                          42

<210> SEQ ID NO 20
<211> LENGTH: 36
<212> TYPE: DNA
<213> ORGANISM: Artificial Sequence
<220> FEATURE:
<223> OTHER INFORMATION: Mpn489 Sig R

<400> SEQUENCE: 20
gtgtgcctgc aggctgccat tggaggtatt gagtgc                                 36

<210> SEQ ID NO 21
<211> LENGTH: 54
<212> TYPE: DNA
<213> ORGANISM: Artificial Sequence
<220> FEATURE:
<223> OTHER INFORMATION: Mpn506 Sig F

<400> SEQUENCE: 21
aagcttgata tcgaattcga ttaaattttc atcttaaaag cttttatttt tacc             54

<210> SEQ ID NO 22
<211> LENGTH: 42
<212> TYPE: DNA
<213> ORGANISM: Artificial Sequence
<220> FEATURE:
<223> OTHER INFORMATION: Mpn506 Sig R

<400> SEQUENCE: 22
gtgtgcctgc aggctgcctt taccctttgt accacaggca gc                          42

<210> SEQ ID NO 23
<211> LENGTH: 49
<212> TYPE: DNA
<213> ORGANISM: Artificial Sequence
<220> FEATURE:
<223> OTHER INFORMATION: Mpn588 Sig F

<400> SEQUENCE: 23
aagcttgata tcgaattctt caattaatca ttgatggttt aagtgtctc                   49

<210> SEQ ID NO 24
<211> LENGTH: 38
<212> TYPE: DNA
<213> ORGANISM: Artificial Sequence
<220> FEATURE:
<223> OTHER INFORMATION: Mpn588 Sig R

<400> SEQUENCE: 24
gtgtgcctgc aggctgccaa agtttggctg ggttgcag                               38

<210> SEQ ID NO 25
<211> LENGTH: 42
<212> TYPE: DNA
<213> ORGANISM: Artificial Sequence
<220> FEATURE:
<223> OTHER INFORMATION: Mpn592 Sig F

<400> SEQUENCE: 25
aagcttgata tcgaattcaa cagacccttta gaagaagtgc ga                         42
```

<210> SEQ ID NO 26
<211> LENGTH: 51
<212> TYPE: DNA
<213> ORGANISM: Artificial Sequence
<220> FEATURE:
<223> OTHER INFORMATION: Mpn592 Sig R

<400> SEQUENCE: 26
gtgtgcctgc aggctgccat ttttgtgatt agtgttagct actgttagcg t            51

<210> SEQ ID NO 27
<211> LENGTH: 60
<212> TYPE: DNA
<213> ORGANISM: Artificial Sequence
<220> FEATURE:
<223> OTHER INFORMATION: Mpn142 only signal_No1

<400> SEQUENCE: 27
tagagacgta attcaaacac atgaaatcga agctaaagtt aaaacgttat ttactgtttt    60

<210> SEQ ID NO 28
<211> LENGTH: 60
<212> TYPE: DNA
<213> ORGANISM: Artificial Sequence
<220> FEATURE:
<223> OTHER INFORMATION: Mpn142 only signal_No2

<400> SEQUENCE: 28
tgttggctag tgacaacgtc cctagcggta aaagtggtaa aaacagtaaa taacgtttta    60

<210> SEQ ID NO 29
<211> LENGTH: 60
<212> TYPE: DNA
<213> ORGANISM: Artificial Sequence
<220> FEATURE:
<223> OTHER INFORMATION: Mpn142 only signal_No3

<400> SEQUENCE: 29
gacgttgtca ctagccaaca cctacctcct ccaaggcagc ctgcagcccg ggggcaaga    60

<210> SEQ ID NO 30
<211> LENGTH: 61
<212> TYPE: DNA
<213> ORGANISM: Artificial Sequence
<220> FEATURE:
<223> OTHER INFORMATION: Mpn645 only signal_No2

<400> SEQUENCE: 30
gtagctgctg aagaacaagc gcttaacaac aaactagaac ctaaaagaga aattaataga    60
a                                                                   61

<210> SEQ ID NO 31
<211> LENGTH: 60
<212> TYPE: DNA
<213> ORGANISM: Artificial Sequence
<220> FEATURE:
<223> OTHER INFORMATION: Mpn645 only signal_No3

<400> SEQUENCE: 31
cgcttgttct tcagcagcta ctcaagtaat ttctggcagc ctgcagcccg ggggcaaga    60

<210> SEQ ID NO 32
<211> LENGTH: 60
<212> TYPE: DNA
<213> ORGANISM: Artificial Sequence
<220> FEATURE:

<223> OTHER INFORMATION: Mpn645 only signal_No1

<400> SEQUENCE: 32
tagagacgta attcaaacac atgaaactga aacttaaatt tctattaatt tctcttttag    60

<210> SEQ ID NO 33
<211> LENGTH: 42
<212> TYPE: DNA
<213> ORGANISM: Artificial Sequence
<220> FEATURE:
<223> OTHER INFORMATION: eFTu Fwd

<400> SEQUENCE: 33
aagcttgata tcgaattcga agacctttg tgctaacgcc ag    42

<210> SEQ ID NO 34
<211> LENGTH: 36
<212> TYPE: DNA
<213> ORGANISM: Artificial Sequence
<220> FEATURE:
<223> OTHER INFORMATION: eFTu Rev

<400> SEQUENCE: 34
gtgtttgaat tacgtctcta attttacata agtttg    36

<210> SEQ ID NO 35
<211> LENGTH: 46
<212> TYPE: DNA
<213> ORGANISM: Artificial Sequence
<220> FEATURE:
<223> OTHER INFORMATION: Mpn459 F

<400> SEQUENCE: 35
gacgtaattc aaacacatgg ctttcatgcc atgtttttca tatagc    46

<210> SEQ ID NO 36
<211> LENGTH: 45
<212> TYPE: DNA
<213> ORGANISM: Artificial Sequence
<220> FEATURE:
<223> OTHER INFORMATION: Mpn459 Rev

<400> SEQUENCE: 36
gtgtgcctgc aggctgccag taacataaac atctcgtgct gggc    45

<210> SEQ ID NO 37
<211> LENGTH: 54
<212> TYPE: DNA
<213> ORGANISM: Artificial Sequence
<220> FEATURE:
<223> OTHER INFORMATION: Mpn213 Rev

<400> SEQUENCE: 37
gtgtgcctgc aggctgcctt ggtgggtctt atttacaagc gttatagttg tagg    54

<210> SEQ ID NO 38
<211> LENGTH: 50
<212> TYPE: DNA
<213> ORGANISM: Artificial Sequence
<220> FEATURE:
<223> OTHER INFORMATION: Mpn213 F

<400> SEQUENCE: 38
gacgtaattc aaacacatga agcttagtgc tattatctcc ctatcagtcg    50

```
<210> SEQ ID NO 39
<211> LENGTH: 16
<212> TYPE: DNA
<213> ORGANISM: Artificial Sequence
<220> FEATURE:
<223> OTHER INFORMATION: Mpn332

<400> SEQUENCE: 39
atgccagctg taaaaa                                                   16

<210> SEQ ID NO 40
<211> LENGTH: 18
<212> TYPE: DNA
<213> ORGANISM: Artificial Sequence
<220> FEATURE:
<223> OTHER INFORMATION: Mpn 332

<400> SEQUENCE: 40
gactaacacc aaacgttt                                                 18
```